United States Patent
Ohnishi et al.

(10) Patent No.: US 7,755,253 B2
(45) Date of Patent: Jul. 13, 2010

(54) PIEZOELECTRIC ELEMENT AND SHAPE OF AN ELECRODE THEREOF

(75) Inventors: Takao Ohnishi, Fuso-Town (JP); Hideki Shimizu, Ohbu (JP); Katsuyuki Tsuneoka, Settsu (JP)

(73) Assignee: NGK Insulators, Ltd., Nagoya-shi (JP)

(*) Notice: Subject to any disclaimer, the term of this patent is extended or adjusted under 35 U.S.C. 154(b) by 0 days.

(21) Appl. No.: 12/241,455

(22) Filed: Sep. 30, 2008

(65) Prior Publication Data
US 2009/0072667 A1    Mar. 19, 2009

Related U.S. Application Data

(63) Continuation of application No. PCT/JP2007/059283, filed on Apr. 23, 2007.

(30) Foreign Application Priority Data

Apr. 24, 2006    (JP)    ............ 2006-119580

(51) Int. Cl.
*H01L 41/08* (2006.01)
(52) U.S. Cl. ............ 310/324; 310/348
(58) Field of Classification Search ............ 310/311, 310/320–322, 324, 348
See application file for complete search history.

(56) References Cited

U.S. PATENT DOCUMENTS

| | | | |
|---|---|---|---|
| 5,889,351 A | 3/1999 | Okumura et al. | |
| 6,541,895 B2 | 4/2003 | Yamaguchi | |
| 7,126,255 B2 | 10/2006 | Yamaguchi et al. | |
| 2008/0315717 A1* | 12/2008 | Schroder et al. | 310/311 |

FOREIGN PATENT DOCUMENTS

| JP | 04-268775 A1 | 9/1992 |
|---|---|---|
| JP | 08-201265 A1 | 8/1996 |
| JP | 2002-261347 A1 | 9/2002 |
| JP | 2004281802 A * | 10/2004 |
| JP | 2005-322890 A1 | 11/2005 |

* cited by examiner

*Primary Examiner*—J. SanMartin
(74) *Attorney, Agent, or Firm*—Burr & Brown (57) ABSTRACT

A piezoelectric/electrostrictive film element includes a substrate, a lower electrode, a piezoelectric/electrostrictive film, and an upper electrode. The substrate has a thin-walled diaphragm portion, and a thick portion formed around the thin-walled diaphragm portion. The lower electrode is formed on the substrate in such a manner as to extend over the thin-walled diaphragm portion and the thick portion. The piezoelectric/electrostrictive film is formed on the lower electrode. The upper electrode is provided on the piezoelectric/electrostrictive film in such a manner as to face the thin-walled diaphragm portion. The upper electrode includes an upper-electrode body portion and a connection portion. The upper-electrode body portion has a planar shape generally similar to the planar shape of the thin-walled diaphragm portion.

5 Claims, 4 Drawing Sheets

PIEZOELECTRIC ELEMENT AND SHAPE OF AN ELECRODE THEREOF

FIELD OF THE INVENTION

The present invention relates to a piezoelectric/electrostrictive film element which utilizes vibration characteristics of its thin-walled diaphragm portion.

BACKGROUND OF THE INVENTION

Known piezoelectric/electrostrictive film elements of this kind include actuators which utilize flexural displacements of their thin-walled diaphragm portions, and sensors (e.g., microphones and viscosity sensors) for detecting characteristics (e.g., fluidal characteristic, sound pressure, very small weight, and acceleration) of media in the proximity of the thin-walled diaphragm portions.

Japanese Patent Application Laid-Open (kokai) Nos. H8-201265 (Patent Document 1), 2002-261347 (Patent Document 2), and 2005-322890 (Patent Document 3) disclose piezoelectric/electrostrictive film elements which serve as the above-mentioned sensors. The piezoelectric/electrostrictive film sensors are configured to be able to utilize the correlation between the amplitude of a piezoelectric/electrostrictive film vibrator and the viscous resistance of fluid in contact with the vibrator and to measure characteristics, such as density, concentration, and viscosity, of the fluid.

Specifically, in the piezoelectric/electrostrictive film sensors, when the vibrator is vibrated in the presence of the fluid, the vibrator is subjected to a dynamic resistance caused by viscosity of the fluid. In the meantime, a mechanical vibrating condition of the vibrator can be replaced with an equivalent electrical circuit. Accordingly, on the basis of viscous resistance to which the vibrator is subjected, an electrical constant of an equivalent circuit of a piezoelectric/electrostrictive film serving as the vibrator varies. By detecting variation of the electrical constant, characteristics, such as viscosity, density, and concentration, of the fluid can be measured.

Fluid whose characteristics can be measured by such the piezoelectric/electrostrictive film sensors encompasses liquid and gas. Examples of liquid serving as an object of measurement include, as a matter of course, a single-component liquid formed solely of a main medium selected from among, for example, water, alcohol, oil, etc. Also, the examples of the object-of-measurement liquid can include a liquid substance (slurry, paste, or the like) formed in such a manner that another medium that is soluble, lightly soluble, or insoluble in such a main medium is added to (dissolved in, mixed with, diffused in, or suspended in) the main medium.

Also, examples of the above-mentioned electrical constant include loss factor, phase, resistance, reactance, conductance, susceptance, inductance, and capacitance. Particularly, phase, or loss factor, which has a single maximal or minimal variation point in the vicinity of the resonance frequency of an equivalent circuit, is preferably used. This enables measurement of density and concentration of the fluid in addition to viscosity of the fluid. For example, the concentration of sulfuric acid in an aqueous solution of sulfuric acid can be measured. In addition to the above-mentioned electrical constants, variation of resonance frequency can be used as an index for detecting variation in vibrating condition, so long as no particular problem arises in terms of accuracy of measurement, and durability.

SUMMARY OF THE INVENTION

This kind of piezoelectric/electrostrictive film element has conventionally had problems with durability. For example, an attempt to improve element characteristics (sensor sensitivity, etc.) through increase in flexural displacement and internal stress of the aforementioned thin-walled diaphragm portion has been accompanied by occurrence of cracking in the aforementioned piezoelectric/electrostrictive film.

The present invention has been conceived for solving the above-mentioned problems. That is, an object of the present invention is to provide a piezoelectric/electrostrictive film element having excellent element characteristics and durability.

A piezoelectric/electrostrictive film element of the present invention comprises a substrate, a lower electrode, a piezoelectric/electrostrictive film, and an upper electrode. The substrate has a thin-walled diaphragm portion, and a thick portion formed around the thin-walled diaphragm portion. The lower electrode is formed on the substrate in such a manner as to extend over the thin-walled diaphragm portion and the thick portion. The piezoelectric/electrostrictive film is formed on the lower electrode. The upper electrode is provided on the piezoelectric/electrostrictive film in such a manner as to face the thin-walled diaphragm portion.

The present invention is characterized in that, in the piezoelectric/electrostrictive film element, the upper electrode comprises an upper-electrode body portion having a planar shape generally similar (i.e., geometrically) to a planar shape of the thin-walled diaphragm portion, and a connection portion provided continuously with the upper-electrode body portion. The upper-electrode body portion is provided in such a manner as to face the thin-walled diaphragm portion. The connection portion has a width narrower than that of the upper-electrode body portion.

In the thus-configured piezoelectric/electrostrictive film element, on the basis of a predetermined input voltage applied between the upper-electrode body portion and the lower electrode, the thin-walled diaphragm portion corresponding to the upper-electrode body portion vibrates. Alternatively, according to a vibrating condition of the thin-walled diaphragm portion and/or variation in the vibrating condition, a predetermined output is generated between the upper-electrode body portion and the lower electrode.

In the present invention, the planar shape of the upper-electrode body portion is generally similar to that of the thin-walled diaphragm portion.

Thus, according to the above-mentioned configuration, on the basis of the input voltage, the thin-walled diaphragm portion can be more efficiently set in a predetermined vibrating condition. Alternatively, a vibrating condition of the thin-walled diaphragm portion can be more efficiently reflected in the output. This enables obtainment of a high output without need to increase an input voltage. Therefore, according to the present invention, the occurrence of cracking in the piezoelectric/electrostrictive film can be restrained, and thus durability can be improved, whereby a more excellent piezoelectric/electrostrictive film element is obtained.

The piezoelectric/electrostrictive film element of the present invention may further comprise an auxiliary electrode. The auxiliary electrode is formed on the substrate in such a manner as to extend over the thick portion and an end portion of the thin-walled diaphragm portion and to be separated from the lower electrode. Further, the auxiliary electrode is connected to the connection portion. Specifically, the piezoelectric/electrostrictive film element is configured as follows.

The lower electrode is formed on the substrate in a region ranging from the thick portion adjacent to a first end of the thin-walled diaphragm portion to a position located toward the first end from an opposite second end of the thin-walled diaphragm portion. Also, the auxiliary electrode is formed on the substrate in a region ranging from the thick portion adjacent to the second end of the thin-walled diaphragm portion to a position located toward the first end from the second end, in such a manner as to be separated from the lower electrode. That is, the lower electrode and the auxiliary electrode are formed on substantially the same plane while being separated from each other by a predetermined gap. The gap is formed at a position located toward the first end from the second end of the thin-walled diaphragm portion; in other words, on the thin-walled diaphragm portion.

The piezoelectric/electrostrictive film is formed on the lower electrode and the auxiliary electrode in such a manner that an end portion of the lower electrode and an end portion of the auxiliary electrode are exposed on the thick portion. Also, the upper-electrode body portion is provided in such a manner as to face the thin-walled diaphragm portion with the lower electrode and the piezoelectric/electrostrictive film intervening therebetween. Further, the connection portion is provided on the piezoelectric/electrostrictive film and the auxiliary electrode so as to connect the upper-electrode body portion and the auxiliary electrode.

In association with vibration or displacement of the thin-walled diaphragm portion, flexural stress is maximized at connections between the thin-walled diaphragm portion and the thick portion; i.e., at the first and second ends of the thin-walled diaphragm portion. If a defect, such as a notch or a very small crack in the form of material discontinuity, is present at a position corresponding to such a connection, stress concentrates at the defect. As a result, a fatigue crack starts from the defect and is developed in the piezoelectric/electrostrictive film. However, in the above-mentioned configuration, the gap is not formed at positions corresponding to the first and second ends of the thin-walled diaphragm portion.

Thus, the above-mentioned configuration can effectively restrain the generation of crack starting from the gap in the piezoelectric/electrostrictive film.

Also, according to the above-mentioned configuration, in a region which is located in the vicinity of the second end of the thin-walled diaphragm portion and which extends over the thin-walled diaphragm portion and the thick portion, the piezoelectric/electrostrictive film is provided between the auxiliary electrode and the upper electrode, which have the same electric potential. That is, in the region in the vicinity of the second end of the thin-walled diaphragm portion, the piezoelectric/electrostrictive film has a portion (inactive portion) to which an electric field is not applied. In other words, a portion of the piezoelectric/electrostrictive film which, upon application of the electric field thereto, causes the thin-walled diaphragm portion to flexurally deform is located toward the "inside" of the thin-walled diaphragm portion from the second end.

Thus, according to the above-mentioned configuration, the thin-walled diaphragm portion can be efficiently excited. Alternatively, at a central portion of the thin-walled diaphragm portion at which the piezoelectric/electrostrictive film exhibits the maximal planar expansion-contraction stress, an output is efficiently generated from between the upper electrode and the lower electrode according to a vibrating condition of the thin-walled diaphragm portion.

The piezoelectric/electrostrictive film element may further comprise an auxiliary connection portion. The auxiliary connection portion is provided for connecting the upper-electrode body portion and the auxiliary electrode.

In the above-mentioned configuration, the upper-electrode body portion and the auxiliary electrode are electrically connected through two independent paths; namely, the connection portion and the auxiliary connection portion.

Thus, according to the above-mentioned configuration, the electrical connection between the upper-electrode body portion and the auxiliary electrode can be more reliably maintained. Accordingly, the durability of the piezoelectric/electrostrictive film element can be further improved.

Preferably, in the piezoelectric/electrostrictive film element of the present invention, a piezoelectric/electrostrictive active portion of the piezoelectric/electrostrictive film, which is a portion of the piezoelectric/electrostrictive film sandwiched between the upper-electrode body portion and the lower electrode, is provided only above the thin-walled diaphragm portion.

In the above-mentioned configuration, the piezoelectric/electrostrictive active portion of the piezoelectric/electrostrictive film, which is a portion of the piezoelectric/electrostrictive film to which an electric field is applied, is present only above the thin-walled diaphragm portion.

Thus, according to the above-mentioned configuration, excitation of the thin-walled diaphragm portion or generation of an output from between the upper electrode and the lower electrode according to a vibrating condition of the thin-walled diaphragm portion can be more efficiently carried out.

More preferably, in the piezoelectric/electrostrictive film element of the present invention, the ratio of a dimension of the piezoelectric/electrostrictive film to a dimension of the thin-walled diaphragm portion with respect to a width direction or a length direction perpendicular to the width direction is 0.95 or less. Specifically, more preferably, as viewed in plane, a major portion of the piezoelectric/electrostrictive film is located at the inside of the outline of the thin-walled diaphragm portion such that, when the width or length of the thin-walled diaphragm portion is taken as 1, the width or length of the piezoelectric/electrostrictive film is 0.95 or less.

In the above-mentioned configuration, end portions of the thin-walled diaphragm portion which are located at the outside of the piezoelectric/electrostrictive film (particularly, the piezoelectric/electrostrictive active portion) can be flexurally deformed in such a condition as to be relatively free from mechanical restraint by the piezoelectric/electrostrictive film.

Thus, according to the above-mentioned configuration, the excitation of the thin-walled diaphragm portion or the generation of output from between the electrodes can be more efficiently carried out. Also, the occurrence of cracking in the piezoelectric/electrostrictive film is restrained; thus, the durability of the piezoelectric/electrostrictive film element can be further improved.

Also, the upper-electrode body portion may have an inactive portion in the form of a through-hole or a cutout.

In the above-mentioned configuration, a region where an applied electric field is weak is formed in the piezoelectric/electrostrictive active portion, which is a portion of the piezoelectric/electrostrictive film sandwiched between the upper-electrode body portion and the lower electrode.

Thus, according to the above-mentioned configuration, stress in the piezoelectric/electrostrictive film associated with expansion and contraction of the piezoelectric/electrostrictive film can be reduced. Accordingly, the occurrence of cracking in the piezoelectric/electrostrictive film is restrained, whereby the durability of the piezoelectric/electrostrictive film element can be further improved.

Preferably, the thin-walled diaphragm portion and the upper-electrode body portion are formed such that an aspect ratio, which is the ratio of length to width, is about 1.2 or greater.

According to the above-mentioned configuration, a flexural displacement of the thin-walled diaphragm portion is increased, whereby more excellent element characteristics are obtained.

BRIEF DESCRIPTION OF THE DRAWINGS

FIG. 1 is a series of views showing the configuration of a piezoelectric/electrostrictive film element for use in a fluid sensor according to an embodiment of the present invention.

DETAILED DESCRIPTION OF THE INVENTION

An embodiment of the present invention (the best mode contemplated by the applicant at the time of filing the present application) will next be described with reference to the drawings. For convenience of providing understandable, consistent description of the embodiment, which is a typical embodiment, the components of the embodiment are described while mentioning their typical structures and the like. Modifications of the structures and the like of the components of the embodiment are described at the end after description of configuration, actions, and effects of the embodiment.

<Configuration of Piezoelectric/electrostrictive Film Element for Use in Sensor>

Figure 1A:
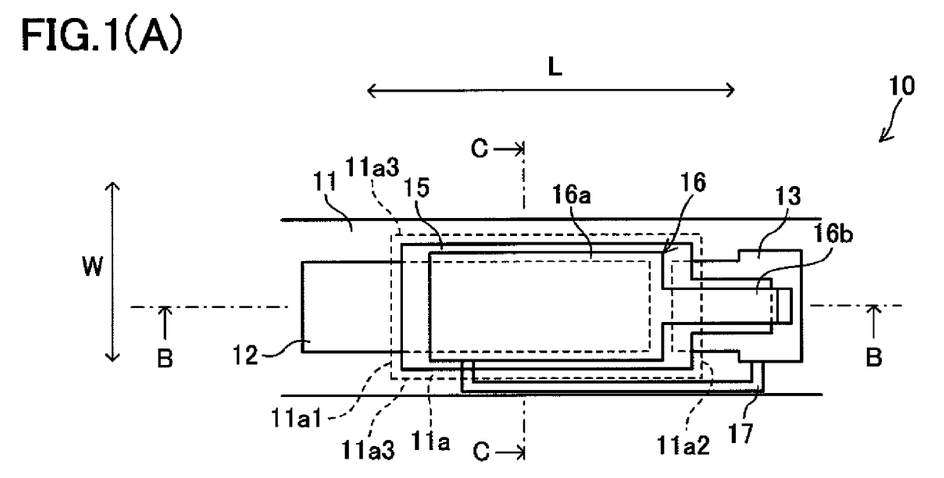
FIG. 1(A) is a plan view of the piezoelectric/electrostrictive film element of the embodiment.
Figure 1B:
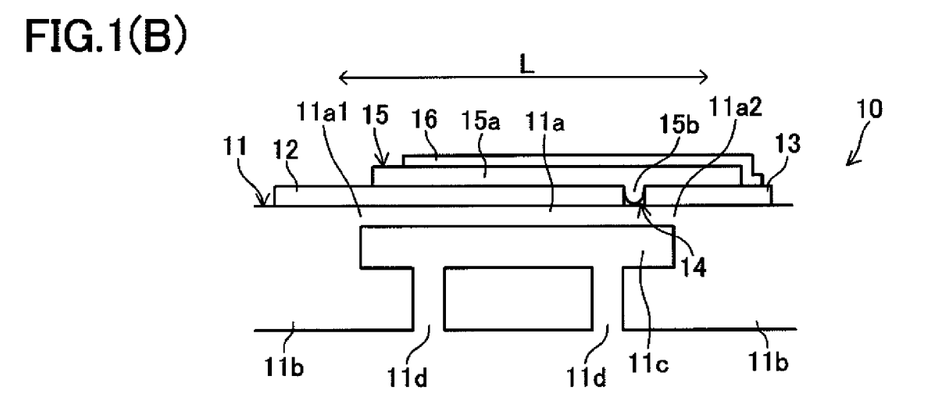
FIG. 1(B) is a sectional view taken along line B-B of FIG. 1(A).
Figure 1C:
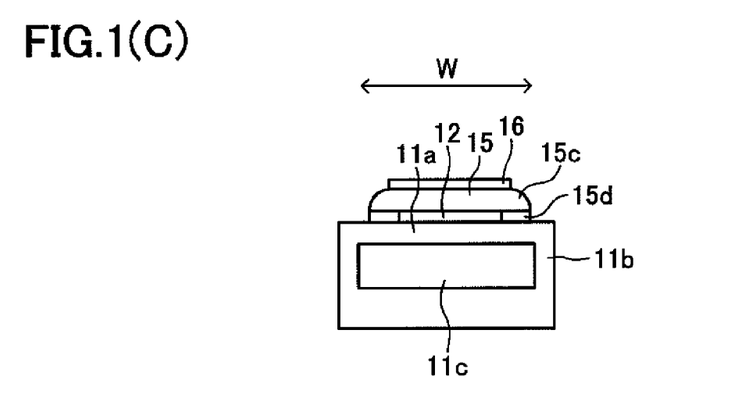
FIG. 1(C) is a sectional view taken along line C-C of FIG. 1(A).

FIG. 1 is a view showing the configuration of a piezoelectric/electrostrictive film element 10 for use in a fluid sensor according to an embodiment of the present invention. FIG. 1(A) is a plan view of the piezoelectric/electrostrictive film element 10 of the present embodiment. FIG. 1(B) is a sectional view taken along line B-B of FIG. 1(A). FIG. 1(C) is a sectional view taken along line C-C of FIG. 1(A).

<<Substrate>>

The piezoelectric/electrostrictive film element 10 includes a substrate 11. The substrate 11 has a thin-walled diaphragm portion 11a. The thin-walled diaphragm portion 11a has a substantially rectangular planar shape for simplifying a resonance mode to be excited. The thin-walled diaphragm portion 11a is configured to be able to be flexurally deformed while a first end 11a1 and a second end 11a2 with respect to its length direction L, and opposite side ends 11a3 with respect to its width direction W serve as fixed ends. The thin-walled diaphragm portion 11a has a thickness of 50 μm or less, preferably 30 μm or less, more preferably 15 μm or less.

The substrate 11 has a thick portion 11b formed around the thin-walled diaphragm portion 11a. The thick portion 11b and the thin-walled diaphragm portion 11a are seamlessly integral with each other. The thick portion 11b is formed sufficiently thick as compared with the thin-walled diaphragm portion 11a.

In view of potential involvement of thermal processing in the course of manufacture of the piezoelectric/electrostrictive film element 10 and potential applications to sensing of characteristics of corrosive fluid, a heat resistant, chemically stable, electrically insulative material is used to form the substrate 11. The substrate 11 is formed of a material selected from among, for example, aluminum oxide, magnesium oxide, mullite, aluminum nitride, silicon nitride, glass, and stabilized zirconium oxide. Of these materials, stabilized zirconium oxide can be preferably used to form the substrate 11, since, even when the thin-walled diaphragm portion 11a is formed thin, it maintains high mechanical strength and exhibits excellent toughness.

The substrate 11 has a cavity 11c and through-holes 11d. The cavity 11c is a hollow portion of the piezoelectric/electrostrictive film 10 of the present embodiment which receives therein an object fluid of sensing. The cavity 11c is formed at a position corresponding to the thin-walled diaphragm portion 11a. The through-holes 11d extend along the thickness direction of the substrate 11. The through-holes 11d are provided in such a manner as to open at the lower surface of the substrate 11, thereby establishing communication between the cavity 11c and the rear side of the substrate 11.

<<Lower Electrode>>

A lower electrode 12 is formed on the upper surface of the substrate 11 in such a manner as to extend over the thin-walled diaphragm portion 11a and the thick portion 11b. Specifically, the lower electrode 12 is formed in a region ranging from the thick portion 11b adjacent to the first end 11a1 of the thin-walled diaphragm portion 11a to a position located toward the first end 11a1 from the second end 11a2 of the thin-walled diaphragm portion 11a. The lower electrode 12 is fixedly bonded to the upper surface of the substrate 11, thereby being provided unitarily with the substrate 11.

The lower electrode 12 is formed of an electrode material which contains, as a main component, platinum, palladium, rhodium, silver, or an alloy thereof. The lower electrode 12 is formed by any of various known film formation processes (for example, thin-film formation processes, such as ion beam process, sputtering, vacuum deposition, CVD, ion plating, and plating, and thick-film formation processes, such as screen printing, spraying, and dipping).

<<Auxiliary Electrode>>

An auxiliary electrode 13 is formed on the upper surface of the substrate 11 in such a manner as to extend over the thick portion 11b and the second end 11a2 of the thin-walled diaphragm portion 11a. Specifically, the auxiliary electrode 13 is formed in a region ranging from the thick portion 11b adjacent to the second end 11a2 of the thin-walled diaphragm portion 11a to a position located toward the first end 11a1 from the second end 11a2 of the thin-walled diaphragm portion 11a. The auxiliary electrode 13 is also fixedly bonded to the upper surface of the substrate 11, thereby being provided unitarily with the substrate 11.

The auxiliary electrode 13 and the lower electrode 12 are provided on substantially the same plane. A predetermined gap 14 is provided between the auxiliary electrode 13 and the lower electrode 12 for electrically insulating them from each other. That is, the auxiliary electrode 13 is provided in such a manner as to be separated from the lower electrode 12 across the gap 14. The gap 14 is provided at a position located toward the first end 11a1 from the second end 11a2 of the thin-walled diaphragm portion 11a; in other words, on the thin-walled diaphragm portion 11a.

The auxiliary electrode 13 is formed of an electrode material which contains, as a main component, platinum, palladium, rhodium, silver, or an alloy thereof. The auxiliary electrode 13 is formed by any of various known film formation processes mentioned above.

<<Piezoelectric/electrostrictive Film>>

A piezoelectric/electrostrictive film 15 is formed on the lower electrode 12 and the auxiliary electrode 13 so as to extend over the lower electrode 12 and the auxiliary electrode 13. The piezoelectric/electrostrictive film 15 is provided in such a manner as to project beyond opposite end portions of the lower electrode 12 with respect to the width direction W.

The piezoelectric/electrostrictive film 15 is fixedly bonded onto the lower electrode 12 and the auxiliary electrode 13, thereby being provided unitarily with the lower electrode 12 and the auxiliary electrode 13. As in the case of the lower electrode 12 and the auxiliary electrode 13 described above, the piezoelectric/electrostrictive film 15 is formed by any of various known film formation processes.

The piezoelectric/electrostrictive film 15 is formed such that an end portion of the lower electrode 12 and an end portion of the auxiliary electrode 13 are exposed on the thick wall portion 11b from its opposite end portions along the length direction L. The end portions of the lower electrode 12 and the auxiliary electrode 13 exposed on the thick portion 11b serve as terminals for the lead connection.

A material which exhibits the piezoelectric/electrostrictive effect is used to form the piezoelectric/electrostrictive film 15. Specifically, the piezoelectric/electrostrictive film 15 is formed from a material selected from among: lead-based ceramic piezoelectric/electrostrictive materials, such as lead zirconate, lead titanate, and lead zirconate titanate (PZT); barium titanate, and barium titanate ceramic ferroelectrics which contain barium titanate as a main component; polymeric piezoelectrics as typified by polyvinylidene fluoride (PVDF); and Bi ceramic piezoelectrics as typified by $(Bi_{0.5}Na_{0.5})TiO_3$. In the case of application to sensors as in the present embodiment, PZT piezoelectrics are most preferably used, because of high piezoelectric characteristics, which enable high-sensitivity detection.

The piezoelectric/electrostrictive film 15 includes a piezoelectric/electrostrictive active portion 15a, an incomplete bond portion 15b, overhang portions 15c, and incomplete bond portions 15d.

The piezoelectric/electrostrictive active portion 15a is a portion sandwiched between the lower electrode 12 and an upper-electrode body portion 16a, which is a major portion of an upper electrode 16 formed on the piezoelectric/electrostrictive film 15. The piezoelectric/electrostrictive active portion 15a is provided only on the thin-walled diaphragm portion 11a.

The incomplete bond portion 15b is provided in such a manner as to project into the gap 14. The incomplete bond portion 15b is incompletely bonded to the substrate 11 (in an incompletely bonded state). Specifically, the incomplete bond portion 15b is incompletely bonded to the substrate 11 such that the peel strength from the substrate 11 is 0.5 kg/mm² or less.

As shown in FIG. 1(C), the overhang portions 15c are end portions of the piezoelectric/electrostrictive film 15 with respect to the width direction W and are provided in such a manner as to laterally project beyond the upper electrode 16. The incomplete bond portions 15d are provided under the overhang portions 15c and laterally cover the lower electrode 12. Similarly to the above-mentioned incomplete bond portion 15b, the incomplete bond portions 15d are incompletely bonded to the substrate 11.

<<Upper Electrode>>

The above-mentioned upper electrode 16 is provided in such a manner as to extend over the piezoelectric/electrostrictive 15 and the auxiliary electrode 13. The upper electrode 16 is fixedly bonded onto the piezoelectric/electrostrictive film 15 and the auxiliary electrode 13, thereby being provided unitarily with the piezoelectric/electrostrictive film 15 and the auxiliary electrode 13. The upper electrode 16 is formed from an electrically conductive material having high bondability in relation to the piezoelectric/electrostrictive film 15 by a film formation process similar to that used to form the lower electrode 12 and the auxiliary electrode 13.

The upper electrode 16 is composed of the upper-electrode body portion 16a and a connection portion 16b.

The upper-electrode body portion 16a is disposed in such a manner as to face the thin-walled diaphragm portion 11a with the lower electrode 12 and the piezoelectric/electrostrictive film 15 intervening therebetween. The upper-electrode body portion 16a has a planar shape generally similar to that of the thin-walled diaphragm portion 11a.

The connection portion 16b has a width narrower than that of the upper-electrode body portion 16a. The connection portion 16b is provided on the piezoelectric/electrostrictive film 15 and the auxiliary electrode 13 so as to connect the upper-electrode body portion 16a and the auxiliary electrode 13. That is, an end portion of the connection portion 16b is seamlessly integral with the upper-electrode body portion 16a so as to be connected with the upper-electrode body portion 16a. The other end portion of the connection portion 16b is bonded to the auxiliary electrode 13, thereby being electrically connected to the auxiliary electrode 13.

Figure 2:
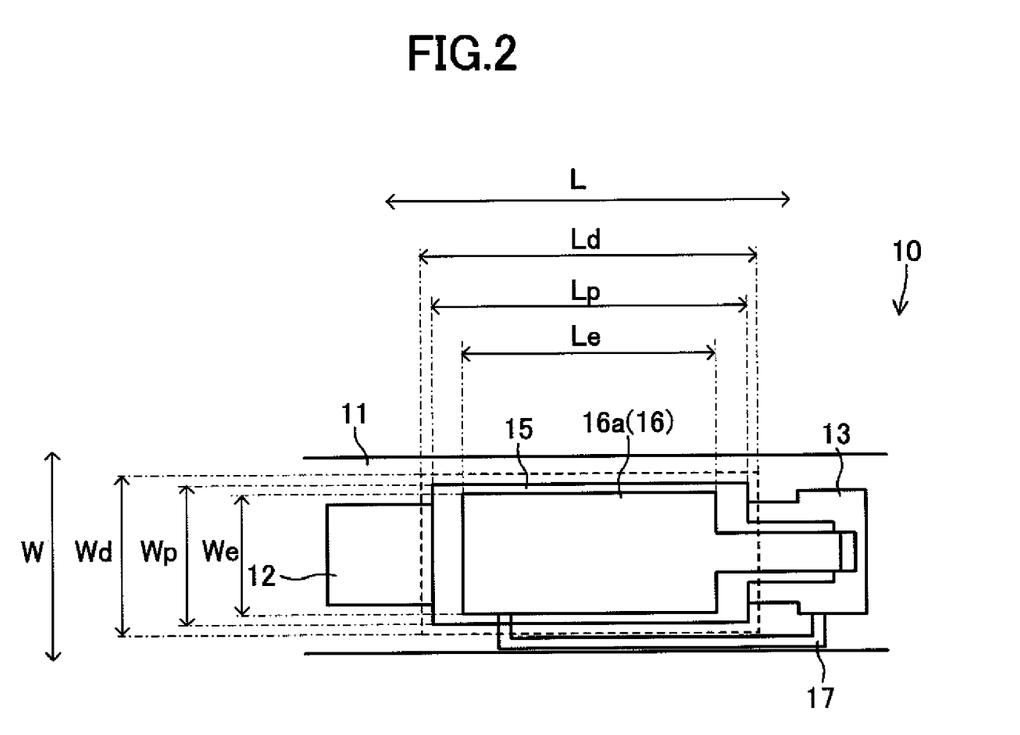
FIG. 2 is a plan view of the piezoelectric/electrostrictive film element shown in FIG. 1.

FIG. 2 is a plan view of the piezoelectric/electrostrictive film element 10 shown in FIG. 1 and corresponds to FIG. 1(A). Referring to FIG. 2, the upper-electrode body portion 16a (along with the thin-walled diaphragm portion 11a) is formed such that an aspect ratio, which is the ratio of length to width, is about 1.2 or greater.

Specifically, the thin-walled diaphragm portion 11a and the upper-electrode body portion 16a are formed such that the ratio of an upper-electrode-body-portion length Le to an upper-electrode-body-portion width We; i.e., an electrode aspect ratio Re=Le/We, is about 1.2 or greater and such that the ratio of a thin-walled-diaphragm-portion length Ld to a thin-walled-diaphragm-portion width Wd; i.e., a diaphragm-portion aspect ratio Rd=Ld/Wd, is about 1.2 or greater.

Also, in the piezoelectric/electrostrictive film element 10 of the present embodiment, the thin-walled diaphragm portion 11a and the piezoelectric/electrostrictive film 15 are formed such that the ratio (Wp/Wd) of a piezoelectric/electrostrictive-film width Wp to the thin-walled-diaphragm-portion width Wd is 0.95 or less and such that the ratio (Lp/Ld) of a piezoelectric/electrostrictive-film length Lp to the thin-walled-diaphragm-portion length Ld is 0.95 or less. That is, as viewed in plane, a major portion (piezoelectric/electrostrictive active portion 15a in FIG. 1) of the piezoelectric/electrostrictive film 15 is located at the inside of the outline of the thin-walled diaphragm portion 11a.

Referring back to FIG. 1, an auxiliary connection portion 17 is provided independently of the connection portion 16b for connecting the upper-electrode body portion 16a and the auxiliary electrode 13. That is, in the piezoelectric/electrostrictive film element 10 of the present embodiment, the upper electrode 16 and the auxiliary electrode 13 are electrically connected through a plurality of independent paths. The auxiliary connection portion 17 is disposed at a greatest possible distance apart from the connection portion 16b.

<Example Method for Manufacturing the Piezoelectric/electrostrictive Film Element of the Embodiment>

Next, an example method for manufacturing the piezoelectric/electrostrictive film element 10 of the present invention will be described.

First, the lower electrode 12 and the auxiliary electrode 13 are formed, by a screen printing process, on the upper surface of the substrate 11 having a predetermined shape mentioned above.

Next, a dummy layer is formed, by a screen printing process, on the upper surface of the substrate 11 at positions corresponding to the incomplete bond portions 15b and 15d so as to prevent direct contact between the substrate 11 and the piezoelectric/electrostrictive film 15. The dummy layer is a film of a synthetic resin and is ablated by burning in thermal processing, which will be described later, for sintering the piezoelectric/electrostrictive film 15.

Subsequently, the piezoelectric/electrostrictive film 15 is formed through an application step which employs a screen printing process, and a thermal processing step for sintering a film applied in the application step. At this time, the above-mentioned dummy layer is ablated, whereby the incomplete bond portions 15b and 15d are formed.

Further, the upper electrode 16 is formed by a screen printing process. Then, a laminate of the upper electrode 16, the piezoelectric/electrostrictive film 15, the auxiliary electrode 13, the lower electrode 12, and the substrate 11 is subjected to thermal processing. By this procedure, the layers of the laminate are firmly bonded and united together.

Finally, a predetermined high voltage is applied between the upper electrode 16 and the lower electrode 12 for polarization of the piezoelectric/electrostrictive film 15.

<Operation of the Piezoelectric/electrostrictive Film Element of the Embodiment>

Next, the operation of the piezoelectric/electrostrictive film element 10 of the present embodiment having the above-described configuration will be described with reference to the drawings.

Fluid to be measured is introduced into the cavity 11c through the through-holes 11d. Fluid which has undergone measurement in the cavity 11c is discharged from the cavity 11c through the through-holes 11d.

When a predetermined drive voltage is applied between the upper electrode 16 and the lower electrode 12, the piezoelectric/electrostrictive active portion 15a of the piezoelectric/electrostrictive film 15 is deformed by converse piezoelectric effect. The deformation of the piezoelectric/electrostrictive film 15 causes the thin-walled diaphragm portion 11a to flexurally deform. Through application of the above-mentioned drive voltage, the thin-walled diaphragm portion 11a is excited at a predetermined resonance frequency.

Fluid contained in the cavity 11c imposes viscous resistance on vibration of the thin-walled diaphragm portion 11a. A vibrating condition of the thin-walled diaphragm portion 11a under the influence of the viscous resistance and variation of the vibrating condition caused by the viscous resistance appear in the form of an expanding-and-contracting condition of the piezoelectric/electrostrictive active portion 15a of the piezoelectric/electrostrictive film 15 sandwiched between the upper electrode 16 and the lower electrode 12 and in the form of variation of the expanding-and-contracting condition. The expanding-and-contracting condition of the piezoelectric/electrostrictive active portion 15a and variation of the expanding-and-contracting condition appear in the form of a waveform of an output voltage generated between the upper electrode 16 and the lower electrode 12 and in the form of variation of the waveform. By analyzing the waveform of the output voltage and variation of the waveform, a characteristic of the fluid-to-be-measured introduced into the cavity 11c can be determined.

<Actions and Effects Yielded by the Configuration of the Embodiment>

Next, actions and effects yielded by the above-described configuration of the piezoelectric/electrostrictive film element 10 of the present embodiment will be described with reference to the drawings.

In the piezoelectric/electrostrictive film element 10 of the present embodiment, the gap 14 and the incomplete bond portion 15b, which serve as material discontinuities, do not overlie the first and second ends 11a1 and 11a2 of the thin-walled diaphragm portion 11a, flexural stress being maximized at the first and second ends 11a1 and 11a2.

The above-mentioned configuration can effectively restrain stress concentration at the first and second ends 11a1 and 11a2 and development of fatigue crack in the piezoelectric/electrostrictive film 15 caused by the stress concentration. Therefore, the durability of the piezoelectric/electrostrictive film element 10 improves.

In the piezoelectric/electrostrictive film element 10 of the present embodiment, the thin-walled diaphragm portion 11a and the upper-electrode body portion 16a are formed generally similar in planar shape. Also, the thin-walled diaphragm portion 11a and the upper-electrode body portion 16a are formed such that the electrode aspect ratio, Re=Le/We, and the diaphragm-portion aspect ratio, Rd=Ld/Wd, are about 1.2 or greater.

According to the above-mentioned configuration, excellent element characteristics (sensor sensibility) are obtained through increase in flexural displacement of the thin-walled diaphragm portion 11a. That is, according to the above-mentioned configuration, on the basis of the above-mentioned drive voltage, the thin-walled diaphragm portion 11a can be more efficiently set in a predetermined vibrating condition. Alternatively, a vibrating condition of the thin-walled diaphragm portion 11a can be more efficiently reflected in the above-mentioned output voltage. Therefore, durability can be improved by means of restraining the occurrence of cracking in the piezoelectric/electrostrictive film 15, and excellent element characteristics are obtained.

In the piezoelectric/electrostrictive film element 10 of the present embodiment, the piezoelectric/electrostrictive active portion 15a is provided only above the thin-walled diaphragm portion 11a. Also, the incomplete bond portions 15b and 15d are provided around the piezoelectric/electrostrictive active portion 15a.

According to the above-mentioned configuration, the bond between the substrate 11 and the piezoelectric/electrostrictive film 15 is mitigated at the overhang portions 15c and the gap 14, whereby the thin-walled diaphragm portion 11a can provide a sufficient flexural displacement and a sufficient amplitude. Also, excitation of the thin-walled diaphragm portion 11a or generation of an output from between the upper electrode 16 and the lower electrode 12 according to a vibrating condition of the thin-walled diaphragm portion 11a can be more efficiently carried out. Therefore, excellent element characteristics (sensor sensibility) are obtained.

In the piezoelectric/electrostrictive film element 10 of the present embodiment, in a region which is located in the vicinity of the second end 11a2 of the thin-walled diaphragm portion 11a and extends over the thin-walled diaphragm portion 11a and the thick portion 11b, the piezoelectric/electrostrictive film 15 is provided between the auxiliary electrode 13 and the upper electrode 16, which have the same electric potential. That is, in the region in the vicinity of the second end 11a2 of the thin-walled diaphragm portion 11a, the piezoelectric/electrostrictive film 15 has a portion (inactive portion) to which an electric field is not applied. In other words, a portion of the piezoelectric/electrostrictive film 15 which, upon application of an electric field thereto, causes the thin-walled diaphragm portion 11a to flexurally deform is located toward the "inside" of the thin-walled diaphragm portion 11a from the second end 11a2.

According to the above-mentioned configuration, the thin-walled diaphragm portion 11a can be efficiently excited. Alternatively, at a central portion of the thin-walled diaphragm portion 11a, at which the piezoelectric/electrostrictive film 15 exhibits the maximal planar expansion-contraction stress, an output voltage is efficiently generated from between the upper electrode 16 and the lower electrode 12 according to a vibrating condition of the thin-walled diaphragm portion 11a. A portion of the piezoelectric/electrostrictive film 15 corresponding to the central region of the thin-walled diaphragm portion 11a exhibits a maximal planar expansion-contraction stress. Thus, excellent element characteristics are obtained. Also, the occurrence of cracking in the piezoelectric/electrostrictive film 15 is restrained; thus, the durability of the piezoelectric/electrostrictive film element 10 is further improved.

In the piezoelectric/electrostrictive film element 10 of the present embodiment, the thin-walled diaphragm portion 11a and the piezoelectric/electrostrictive film 15 are formed such that the ratio (Wd/Wp) of the piezoelectric/electrostrictive-film width Wp to the thin-walled-diaphragm-portion width Wd and the ratio (Ld/Lp) of the piezoelectric/electrostrictive-film length Lp to the thin-walled-diaphragm-portion length Ld are 0.95 or less.

According to the above-mentioned configuration, end portions of the thin-walled diaphragm portion 11a which are located at the outside of the piezoelectric/electrostrictive film 15 (particularly, the piezoelectric/electrostrictive active portion 15a) can be flexurally deformed in such a condition as to be relatively free from mechanical restraint by the piezoelectric/electrostrictive film 15. Thus, the excitation of the thin-walled diaphragm portion 11a or the generation of output from between the electrodes can be more efficiently carried out. Also, the occurrence of cracking in the piezoelectric/electrostrictive film 15 is restrained; thus, the durability of the piezoelectric/electrostrictive film element 10 can be further improved.

In the piezoelectric/electrostrictive film element 10 of the present embodiment, the upper-electrode body portion 16a and the auxiliary electrode 13 are electrically connected through two independent paths; namely, the connection portion 16b and the auxiliary connection portion 17.

According to the above-mentioned configuration, even when, for example, a deterioration in insulating properties of the piezoelectric/electrostrictive film 15 causes damage to a portion of the upper electrode 16 with a resultant breakage of the connection portion 16b of the upper-electrode body portion 16a, an electrical connection between the upper-electrode body portion 16a and the auxiliary electrode 13 can be maintained through the auxiliary connection portion 17. Thus, according to the configuration of the present embodiment, an electrical connection between the upper-electrode body portion 16a and the auxiliary electrode 13 can be more reliably maintained. Therefore, the durability of the piezoelectric/electrostrictive film element 10 can be further improved.

In the piezoelectric/electrostrictive film element 10 of the present embodiment, the piezoelectric/electrostrictive film 15 is provided in such a manner as to cover opposite end portions of the lower electrode 12 with respect to the width direction W. This eliminates need for accurate positioning between the lower electrode 12 and the piezoelectric/electrostrictive film 15, whereby manufacturing cost can be reduced. Also, a short circuit between the lower electrode 12 and the upper electrode 16 can be effectively restrained by means of a simple device configuration.

<Modifications>

The above-described embodiment is, as mentioned previously, a mere example of the best mode which the applicant of the present invention contemplated at the time of filing the present application. The present invention is not limited to the above-described embodiment. Various modifications to the above-described embodiment are possible so long as the invention is not modified in essence.

Typical modifications will next be exemplified. In the following description of the modifications, members similar in structure and function to those used in the above-described embodiment can be denoted by the same reference numerals as those of the above-described embodiment As for the description of these members, an associated description appearing in the description of the above-described embodiment can be cited so long as no technical inconsistencies are involved.

Needless to say, even modifications are not limited to those exemplified below. The following modifications are applicable in appropriate combination so long as no technical inconsistencies are involved.

The above-described embodiment and the following modifications should not be construed as limiting the present invention (particularly, those components which partially constitute means for solving the problems to be solved by the invention and are illustrated with respect to operations and functions). (Such limiting construal unfairly impairs the interests of an applicant who is motivated to file as quickly as possible under the first-to-file system; unfairly benefits imitators; is adverse to the purpose of the Patent Law of protecting and utilizing an invention; and is thus impermissible.)

(1) Applications of the present invention are not limited to sensor elements as in the case of the above embodiment. For example, the present invention can be applied to actuators.

(2) The planar shape of the thin-walled diaphragm portion 11a and the upper-electrode body portion 16a can be any shape, such as a rectangular shape, a square shape, a triangular shape, an elliptical shape, or a true circular shape. However, in the piezoelectric/electrostrictive film element 10 for use as a sensor element in which a resonance mode to be excited must be simplified, a rectangular shape or a true circular shape is selected as needed.

(3) No particular limitation is imposed on the shape of the cavity 11c and on the number, arrangement, and structure of the through-holes 11d communicating with the cavity 11c.

Alternatively, the cavity 11c may be formed such that substantially the entire thin-walled diaphragm portion 11a is exposed toward the side of the lower surface of the substrate 11. That is, there may be formed a single through-hole 11d whose shape of opening as viewed in plane is substantially the same as the planar shape of the thin-walled diaphragm portion 11a.

(4) Different materials or the same material may be used to form the lower electrode 12, the auxiliary electrode 13, and the upper electrode 16.

A most preferred material for the lower electrode 12 and the auxiliary electrode 13 is an electrically conductive material having good bondability in relation to both of the substrate 11 and the piezoelectric/electrostrictive film 15. Particularly, in the case where a thermal processing step for sintering is carried out in the course of formation of the piezoelectric/electrostrictive film 15, platinum or an alloy which contains platinum as a main component is preferably used.

Also, a most preferred material for the upper electrode 16 is an electrically conductive material having good bondability in relation to both of the auxiliary electrode 13 and the piezoelectric/electrostrictive film 15.

(5) The piezoelectric/electrostrictive film 15 may be formed in such a manner as to not overlie the thick portion 11b. Specifically, the piezoelectric/electrostrictive film 15 may be formed such that its end portion on the side toward the auxiliary electrode 13 is located toward the first end 11a1 (toward the inside of the thin-walled diaphragm portion 11a) from the second end 11a2, which is an end of the thin-walled diaphragm portion 11a on the side toward the auxiliary electrode 13.

(6) The materials mentioned above in the description of the embodiment are used singly, or in combination for improving piezoelectric/electrostrictive characteristics, to form the piezoelectric/electrostrictive film 15. Alternatively, in order to improve piezoelectric/electrostrictive characteristics, another additive(s) may be added as appropriate. The above-mentioned composite materials can be used in the form of mixtures or solid solutions.

Particularly, a preferred material for the piezoelectric/electrostrictive film 15 contains, as a main component, one or more components selected from among lead titanate, lead zirconate, magnesium lead niobate, and nickel lead niobate. The reason for this is that, since their reactivity in relation to a material used to form the substrate 11 is low and since segregation of components is unlikely to occur during thermal processing, a desired composition and a desired crystal structure can be readily attained.

Also, in the case where platinum or an alloy which contains platinum as a main component is used to form the lower electrode 12 and the auxiliary electrode 13, $(Bi_{0.5}Na_{0.5})TiO_3$ or a material which contains $(Bi_{0.5}Na_{0.5})TiO_3$ as a main component is preferably used to form the piezoelectric/electrostrictive film 15, since such a material exhibits higher bondability in relation to platinum and the alloy and lowers variation of characteristics among elements to thereby impart high reliability to the elements. Of these materials, particularly, $(1-x)(Bi_{0.5}Na_{0.5})TiO_3\text{-}xKNbO_3$ (x is mol fraction; $0 \leq x \leq 0.06$) or a material which contains $(1-x)(Bi_{0.5}Na_{0.5})TiO_3\text{-}xKNbO_3$ as a main component is more preferably used, since such a material has relatively high piezoelectric characteristic.

In this case, preferably, the formed piezoelectric/electrostrictive film 15 is subjected to thermal processing at a temperature of 900° C. to 1,400° C. inclusive, preferably 1,000° C. to 1,300° C. inclusive (the same convention is applied to the case where a PZT material is used to form the piezoelectric/electrostrictive film 15). In this case, in order to prevent the piezoelectric/electrostrictive film 15 from becoming unstable at high temperature, preferably, the thermal processing is carried out while controlling atmosphere as well as a piezoelectric/electrostrictive material evaporation source.

(7) A stamping process and an ink jet process as well as a screen printing process can be preferably used to form the above-mentioned dummy layer, which is used to establish the above-mentioned incompletely bonded state as in the incomplete bond portion 15b and the like.

In the case where no thermal processing is performed in the course of formation of the piezoelectric/electrostrictive film 15, the upper electrode 16, etc., the dummy layer can be formed by use of a material (synthetic resin or the like) which dissolves in water, an organic solvent, etc. In this case, after formation of the piezoelectric/electrostrictive film 15 or after formation of the upper electrode 16, the dummy layer is dissolvingly eliminated by use of water, an organic solvent, or the like, thereby forming the incomplete bond portion 15b and the like.

Also, by means of appropriately adjusting materials and film formation conditions for the substrate 11 and the piezoelectric/electrostrictive film 15, the incomplete bond portion 15b and the like can be formed without use of the above-mentioned dummy layer.

(8) The incomplete bond portion 15b and the like may be in an unbonded state; i.e., may be completely unbonded to the substrate 11.

(9) The overhang portions 15c and the incomplete bond portions 15d located under the overhang portions 15c can be eliminated. In the case where variation of an electrical constant, which serves as an element characteristic, among elements, and time-course variation of an electrical constant must further be reduced, substantially the same size may be imparted to the lower electrode 12 and the piezoelectric/electrostrictive film 15. In this case, the overhang portions 15c are not formed. Also, the lower electrode 12 may be formed greater than the piezoelectric/electrostrictive 15.

Figure 3:
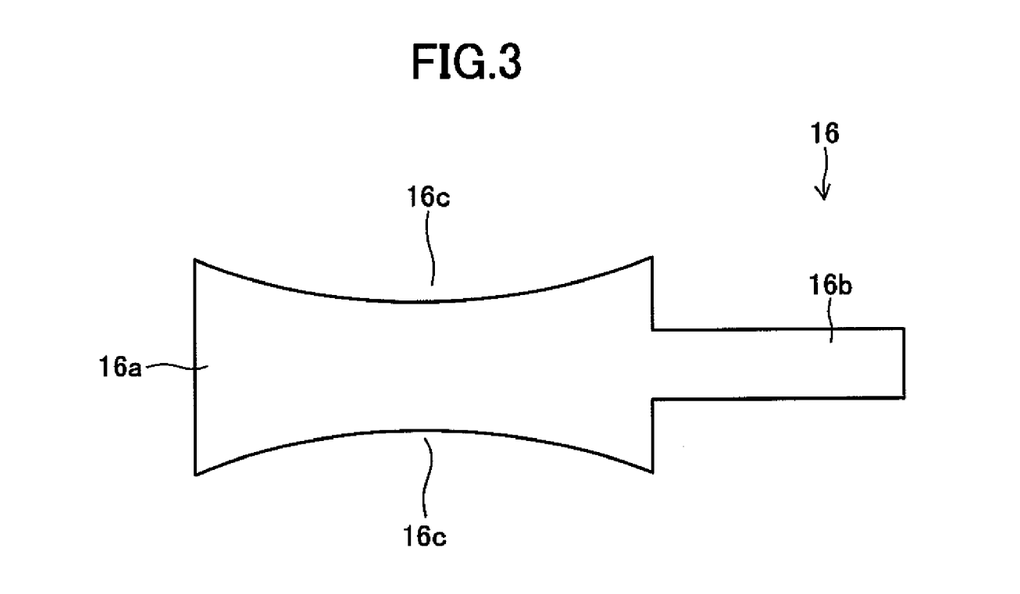
FIG. 3 is a plan view showing a modification of the configuration of an upper electrode shown in FIG. 1.

(10) FIG. 3 is a plan view showing the configuration of a modification of the upper electrode 16 shown in FIG. 1. As shown in FIG. 31 the upper-electrode body portion 16a has inactive portions 16c in the form of cutouts. The inactive portions 16c are formed by cutting out opposite ends of the upper-electrode body portion 16a with respect to the width direction (substantially perpendicular to a direction along which the connection portion 16b extends).

Referring to FIGS. 1 and 3, in the above-mentioned configuration, a region where an applied electric field is weak is formed in the piezoelectric/electrostrictive active portion 15a, which is a portion of the piezoelectric/electrostrictive film 15 sandwiched between the upper-electrode body portion 16a and the lower electrode 12.

Thus, according to the above-mentioned configuration, stress in the piezoelectric/electrostrictive film 15 associated with expansion and contraction of the piezoelectric/electrostrictive film 15 can be reduced. Accordingly, the occurrence of cracking in the piezoelectric/electrostrictive film 15 is restrained, whereby the durability of the piezoelectric/electrostrictive film element 10 can be further improved.

Figure 4:
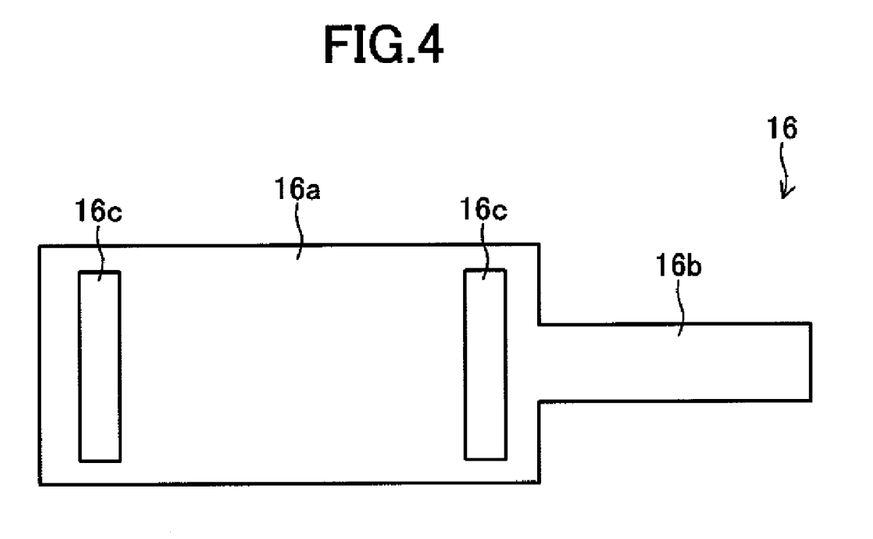
FIG. 4 is a plan view showing another modification of the configuration of an upper electrode shown in FIG. 3.

(11) FIG. 4 is a plan view showing the configuration of another modification of the upper electrode 16 shown in FIG. 3. As shown in FIG. 4, the upper-electrode body portion 16a may have the inactive portions 16c in the form of through-holes. In the present modification, the inactive portions 16c in the form of through-holes are provided at opposite end portions of the upper-electrode body portion 16a with respect to the length direction (along which the connection portion 16b extends).

As in the case of the above-mentioned modification shown in FIG. 3, according to the above-mentioned configuration, the occurrence of cracking in the piezoelectric/electrostrictive film 15 is restrained, whereby the durability of the piezoelectric/electrostrictive film element 10 can be further improved.

Figure 5:
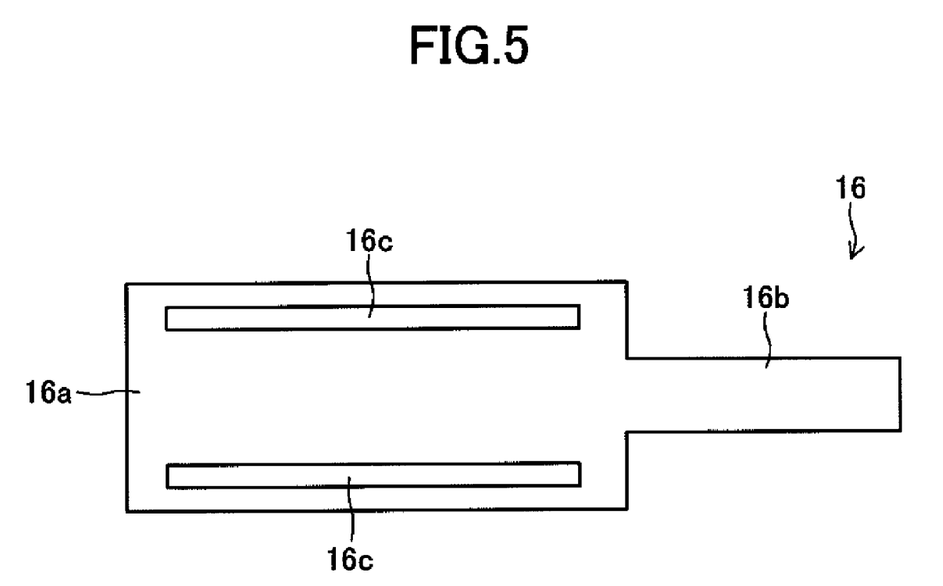
FIG. 5 is a plan view showing still another modification of the configuration of the upper electrode shown in FIG. 3.

(12) FIG. 5 is a plan view showing the configuration of still another modification of the upper electrode 16 shown in FIG. 3. As shown in FIG. 5, the inactive portions 16c in the form of through-holes may be formed. In the present modification, the inactive portions 16c in the form of through-holes are provided at opposite end portions of the upper-electrode body portion 16a with respect to the width direction (substantially perpendicular to a direction along which the connection portion 16b extends).

As in the case of the above-mentioned modifications shown in FIGS. 3 and 4, according to the above-mentioned configuration, the occurrence of cracking in the piezoelectric/electrostrictive film 15 is restrained, whereby the durability of the piezoelectric/electrostrictive film element 10 can be further improved.

Figure 6:
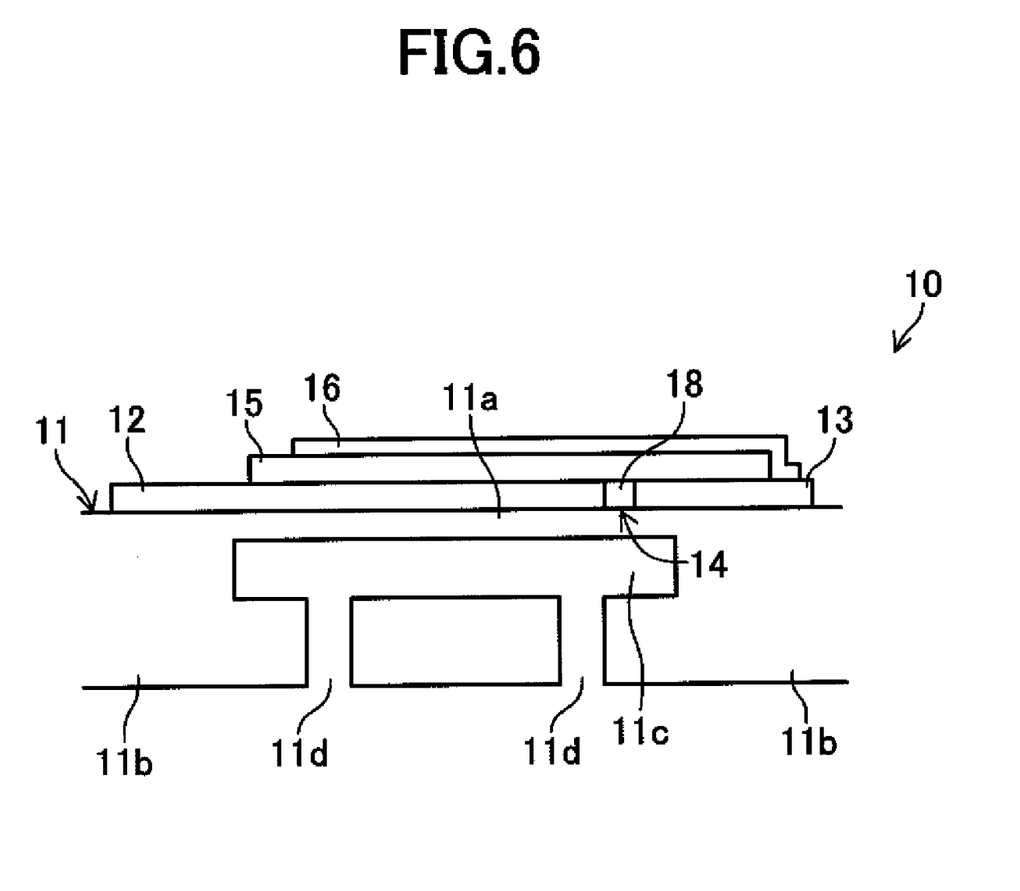
FIG. 6 is a sectional view showing a modification of the configuration of the periphery of a gap between a lower electrode and an auxiliary electrode in the piezoelectric/electrostrictive film element shown in FIG. 1.

(13) FIG. 6 is a sectional view showing a modification of the configuration of the periphery of the gap 14 between the lower electrode 12 and the auxiliary electrode 13 in the piezoelectric/electrostrictive film element 10 shown in FIG. 1.

Referring to FIG. 6, in the present modification, a bond layer 18 for bonding the piezoelectric/electrostrictive film 15 and the thin-walled diaphragm portion 11a is provided in the gap 14 between the lower electrode 12 and the auxiliary electrode 13. The bond layer 18 is formed from an insulator.

In the above-mentioned configuration, the piezoelectric/electrostrictive film 15 and the substrate 11 are in a completely bonded state at the position of the gap 14 between the lower electrode 12 and the auxiliary electrode 13. This stabilizes a vibrating condition of the thin-walled diaphragm portion 11a. Accordingly, element characteristics of the piezoelectric/electrostrictive film element 10 can be further improved.

In the case where the bond layer 18 is provided, prior to formation of the piezoelectric/electrostrictive film 15, the bond layer 18 is formed in the gap 14. An ordinary thick-film formation process can be used to form the bond layer 18. Particularly, a stamping process or a screen printing process can be preferably used. In the case where a portion to be formed has a size of several tens μmm to several hundreds μmm, an ink jet process can be preferably used. After formation of the piezoelectric/electrostrictive 15, thermal processing is performed as needed, whereby the piezoelectric/electrostrictive film 15, the lower electrode 12, the auxiliary electrode 13, and the bond layer 18 are united together.

A material having high adhesion and high bondability in relation to the piezoelectric/electrostrictive film 15 and the substrate 11 can be preferably used to form the bond layer 18. For example, in addition to an inorganic material, such as glass, an organic material can be preferably used. In the case where a thermal processing step for sintering is carried out in the course of formation of the piezoelectric/electrostrictive film 15, a glass material can be used as a material for forming the bond layer 18. Particularly, a glass material having a softening point equal to or higher than a thermal processing temperature for the piezoelectric/electrostrictive film 15 is more preferably used, since the glass material can more firmly bond the piezoelectric/electrostrictive film 15 and the substrate 11 and since its deformation which could otherwise result from thermal processing can be restrained, because of its high softening point.

More preferably, in view of attainment of bondability with high reliability, the thermal expansion coefficient of a material used to form the bond layer 18 assumes an intermediate value between the thermal expansion coefficient of a material used to form the ceramic substrate 11 and the thermal expansion coefficient of a material used to form the piezoelectric/electrostrictive film 15.

Further, in the case where the piezoelectric/electrostrictive film 15 is formed from the above-mentioned $(Bi_{0.5}Na_{0.5})TiO_3$ or a material which contains $(Bi_{0.5}Na_{0.5})TiO_3$ as a main component, a material which contains $(1-x)(Bi_{0.5}Na_{0.5})TiO_3$-$xKNbO_3$ (x is mol fraction; $0.08 \leq x \leq 0.5$) as a main component can be more preferably selected to form the bond layer 18.

In this case, the material used to form the bond layer 18 and the material used to form the piezoelectric/electrostrictive film 15 contain a similar component. Accordingly, adhesion between the bond layer 18 and the piezoelectric/electrostrictive film 15 is improved. Also, as compared with the case where a glass material is used to form the bond layer 18, susceptibility to a problem caused by diffusion of foreign elements is lowered. Further, since the material used to form the bond layer 18 contains a large amount of $KNbO_3$, reactivity in relation to the substrate 11 is enhanced, so that the bond layer 18 can be strongly bonded to the substrate 11.

Further, $(1-x)(Bi_{0.5}Na_{0.5})TiO_3$-$xKNbO_3$ (x is mol fraction; $0.08 \leq x \leq 0.5$), which forms the bond layer 18, exhibits little piezoelectric characteristic. Accordingly, the generation of vibration and displacement of and stress in the bond layer 18 is restrained. Such a generation of vibration, displacement, and stress is caused by an electric field generated between the lower electrode 12 and the auxiliary electrode 13 at the time of use. Therefore, consistent element characteristics can be obtained.

(14) The lower electrode 12, the auxiliary electrode 13, the piezoelectric/electrostrictive film 15, and the upper electrode 16 (along with the bond layer 18) are strongly bonded into a unitary structure through thermal processing Thermal processing may be performed each time each of the layers is formed. Alternatively, after all of the layers are formed, the layers may be subjected to thermal processing at a time. Needless to say, when thermal processing is performed, a proper thermal processing temperature is employed in order to attain good bondability and to restrain degeneration, which could otherwise result from diffusion of component elements.

When thermal processing needs to be performed on the bond layer 18, the bond layer 18 may be subjected to thermal processing before a next step of forming the piezoelectric/electrostrictive film 15. Alternatively, after the piezoelectric/electrostrictive film 15 is formed, the bond layer 18 and the piezoelectric/electrostrictive film 15 may be simultaneously subjected to thermal processing.

(15) Those components which partially constitute means for solving the problems to be solved by the invention and are illustrated with respect to operations and functions encompass not only the specific structures disclosed above in the description of the above embodiment and modifications but also any other structures that can implement the operations and functions.

The invention claimed is:
1. A piezoelectric/electrostrictive film element comprising:

a substrate having a thin-walled diaphragm portion, and a thick portion formed around the thin-walled diaphragm portion;

a lower electrode formed on the substrate in such a manner as to extend over the thin-walled diaphragm portion and the thick portion;

a piezoelectric/electrostrictive film formed on the lower electrode; and an upper electrode comprising an upper-electrode body portion having a planar shape geometrically similar to a planar shape of the thin-walled diaphragm portion and provided on the piezoelectric/electrostrictive film in such a manner as to face the thin-walled diaphragm portion, and a connection portion provided on the piezoelectric/electrostrictive film continuously with the upper-electrode body portion and having a width narrower than that of the upper-electrode body portion.

2. A piezoelectric/electrostrictive film element according to claim 1, further comprising:

an auxiliary electrode connected to the connection portion and formed on the substrate in such a manner as to extend over the thick portion and an end portion of the thin-walled diaphragm portion and to be separated from the lower electrode, and an auxiliary connection portion provided for connecting the upper-electrode body portion and the auxiliary electrode.

3. A piezoelectric/electrostrictive film element according to claim 1, wherein the piezoelectric/electrostrictive film is formed such that the ratio of a dimension of the piezoelectric/electrostrictive film to a dimension of the thin-walled diaphragm portion with respect to a width direction or a length direction perpendicular to the width direction is 0.95 or less.

4. A piezoelectric/electrostrictive film element according to claim 1, wherein the upper-electrode body portion has an inactive portion in the form of a through-hole or a cutout.

5. A piezoelectric/electrostrictive film element according to claim 1, wherein the thin-walled diaphragm portion and the upper-electrode body portion are formed such that an aspect ratio, which is the ratio of length to width, is about 1.2 or greater.

* * * * *